(12) United States Patent
Kawamura et al.

(10) Patent No.: US 7,314,643 B2
(45) Date of Patent: Jan. 1, 2008

(54) SOFT CAPSULE PREPARATION

(75) Inventors: Reiko Kawamura, Saitama (JP); Yuya Egawa, Kounosu (JP)

(73) Assignees: Nikken Chemicals Co., Ltd., Tokyo (JP); Leber Co., Ltd., Tokyo (JP)

( * ) Notice: Subject to any disclaimer, the term of this patent is extended or adjusted under 35 U.S.C. 154(b) by 45 days.

(21) Appl. No.: 10/524,420

(22) PCT Filed: Aug. 19, 2003

(86) PCT No.: PCT/JP03/10440

§ 371 (c)(1),
(2), (4) Date: Oct. 11, 2005

(87) PCT Pub. No.: WO2004/017958

PCT Pub. Date: Mar. 4, 2004

(65) Prior Publication Data

US 2006/0141022 A1    Jun. 29, 2006

(30) Foreign Application Priority Data

Aug. 20, 2002 (JP) .............................. 2002-239584

(51) Int. Cl.
*A61K 36/00* (2006.01)
(52) U.S. Cl. .................................................... 424/757
(58) Field of Classification Search .................. None
See application file for complete search history.

(56) References Cited

U.S. PATENT DOCUMENTS

| 4,346,109 | A | | 8/1982 | Yamatsu et al. |
| 4,491,592 | A | * | 1/1985 | Katoh et al. ............... 514/560 |
| 4,655,973 | A | | 4/1987 | Yamatsu et al. |
| 4,757,140 | A | | 7/1988 | DeLuca et al. |
| 4,788,330 | A | | 11/1988 | Nakamoto et al. |
| 4,841,038 | A | | 6/1989 | DeLuca et al. |
| 4,883,916 | A | | 11/1989 | Nakamoto et al. |
| 4,888,439 | A | | 12/1989 | Yamatsu et al. |
| 4,917,829 | A | | 4/1990 | Yamatsu et al. |
| 4,988,732 | A | | 1/1991 | Yamatsu et al. |
| 5,852,057 | A | * | 12/1998 | Muto et al. ................ 514/560 |
| 5,891,470 | A | * | 4/1999 | Rinaldi et al. .............. 424/451 |
| 6,369,251 | B1 | | 4/2002 | Takano et al. |
| 6,984,742 | B2 | | 1/2006 | Tanikawa et al. |
| 2005/0250671 | A1 | | 11/2005 | Shidoji et al. |
| 2006/0063838 | A1 | | 3/2006 | Shidoji et al. |
| 2006/0094784 | A1 | | 5/2006 | Kagawa et al. |

FOREIGN PATENT DOCUMENTS

| EP | 0054732 | 6/1982 |
| EP | 0194693 | 9/1986 |
| EP | 0847754 | 6/1998 |
| EP | 1046630 | 3/2003 |
| GB | 781809 | 8/1957 |
| JP | 54-46821 | 4/1979 |
| JP | 55-22645 | 2/1980 |
| JP | 55-138457 | 10/1980 |
| JP | 63-32058 | 4/1981 |
| JP | 56-140949 | 11/1981 |
| JP | 57-106638 | 7/1982 |
| JP | 58-109415 | 6/1983 |
| JP | 62-77317 | 4/1987 |
| JP | 63-32058 | 6/1988 |
| JP | 63-34855 | 7/1988 |
| JP | 63-166824 | * 7/1988 |
| JP | 10-167960 | 6/1998 |
| JP | 2000-122974 | 4/2000 |
| WO | 94/22818 | 10/1994 |
| WO | 01/15702 | 3/2001 |
| WO | 01/80854 | 11/2001 |
| WO | 03/097034 | 11/2003 |

OTHER PUBLICATIONS

1996. Muto et al. New England Journal of Medicine. vol. 334. No. 24 pp. 1561-1567.*
Nariaki Nakamura et al., "Apoptosis in Human Hepatoma Cell Line Induced by 4,5-Didehydrogeranylgeranoic Acid (Acyclic Retinoid) Via Down-Regulation of Transforming Growth Factor-α," Biochemical and Biophysical Research Communications, vol. 219, No. 1, pp. 100-104 (1996).
M. Okuno et al., "Retinoids Exacerbate Rat Liver Fibrosis by Inducing the Activation of latent TGF-β in Liver Stellate Cells," Hepatology (Philadelphia), vol. 26, No. 4, pp. 913-921 (1997).
Di Bisceglie A.M. et al., "Hepatocellular Carcinoma," Hepatology, vol. 28, No. 4, pp. 1161-1165 (1998).
Ishiwari, K., "The Effects of a Synthetic Retinoid on Phenotypic Expression of Cultured Mesangial Cells," Kyoto-furitsu Ika Daigaku Zasshi, vol. 106, No. 3, pp. 273-283 (1997).
P. Ellinghaus et al., "Phytanic Acid Activates the Peroxisome Proliferator-Activated Receptor α(PPARα) in Sterol Carrier Protein 2-/Sterol Carrier Protein x-deficient Mice," J. Biol. Chem., vol. 274, No. 5, pp. 2766-2772 (Jan. 29, 1999).
S.A. Kliewer et al., "Fatty acids and eicosanoids regulate gene expression through direct interactions with peroxisome proliferators-activated receptors α and Γ ," Proc. Natl. Acad. Sci. U.S.A., vol. 94, No. 9, pp. 4318-4323 (Apr. 1997).
M. Göttlicher et al., "Structural and Metabolic Requirements for Activators of the Peroxisome Proliferator-Activated Receptor," Biochem. Pharmacol., vol. 46, No. 12, pp. 2177-2184 (1993).
I. Issemann et al., "The peroxisome proliferators-activated receptor-:retinoid X receptor heterodimer is activated by fatty acids and fibrate hypolipidaemic drugs," J. Mol. Endocrinol., vol. 11, No. 1, pp. 37-47 (1993).

(Continued)

Primary Examiner—Christopher R. Tate
Assistant Examiner—Melenie McCormick
(74) Attorney, Agent, or Firm—Greenblum & Bernstein, P.L.C.

(57) ABSTRACT

A soft capsule preparation which comprises a dispersion of (2E,4E,6E,10E)-3,7,11,15-tetramethyl-2,4,6,10,14-hexadecapentaenoic acid in a vegetable oil filled in a soft capsule comprising a shell having a light blocking effect. The soft capsule preparation preferably comprises polyoxyethylene sorbitan monooleate and glycerol monostearate and the like as surfactants. As the vegetable oil, soybean oil, sesame oil, a mixture thereof, or the like may be used.

6 Claims, No Drawings

OTHER PUBLICATIONS

G.M. Reaven, "Role of Insulin Resistance in Human Disease," Diabetes, vol. 37, pp. 1595-1607 (1988).

I. Issemann et al., "Activation of a member of the steroid hormone receptor superfamily by peroxisome proliferators," Nature, vol. 347, pp. 645-650 (1990).

J.M. Lehmann et al., "An Antidiabetic Thiozolidinedione Is a High Affinity Ligand for Peroxisome Proliferator-activated Receptor Γ(PPARΓ)," J. Biol. Chem. vol. 270, No. 22, pp. 12953-12956 (1995).

A.R. Saltiel et al., "Thiozolidinediones in the Treatment of Insulin Resistance and Type II Diabetes," Diabetes, vol. 45, pp. 1661-1669 (1996).

Rinshu Iyaku, "Liver Dysfunction Associated with Troglitazone (Noscal®)," vol. 14, pp. 461-466 (1998).

Remington: The Science and Practice of Pharmacy, Mack Publishing Co., Nineteenth Edition, vol. 1, Chapter 48, "The Introduction of New Drugs", pp. 795-808 (1995).

K. Tago et al., "A Practical Total Synthesis of Plaunotol via Highly Z-selective Wittig Olefination of α-acetal ketones," J. Chem. Soc. Perkin Trans. 1, pp. 2073-2078 (2000).

W.C. Still et al., "Direct Synthesis of Z-Unsaturated Esters. A Useful Modification of the Horner-Emmons Olefination," Tetrahedron Letters, vol. 24, No. 41, pp. 4405-4408 (1983).

T. Kajiwara et al., "Stereoselective Synthesis of Ectocarpene and Its Antipode via Microbiological Asymmetric Hydrolysis," Agric. Biol. Chem., vol. 45, pp. 1461-1466 (1981).

Chinese Journal of Applied Chemistry, vol. 5, 1988, pp. 70-71.

R. Boden, "A Mild Method for Preparing trans-Alkenes; Crown Ether Catalysis of the Wittig Reaction," Synthesis, p. 784 (1975).

G. Bellucci et al., "Crown Ether Catalyzed Stereospecific Synthesis of Z- and E-Stilbenes by Wittig Reaction in a Solid-Liquid Two-Phases System," Tetrahedron Letters, vol. 37, No. 24, pp. 4225-4228 (1996).

G. Bellucci et al., "Crown Ether Catalyzed Stereospecific Synthesis of Z- and E-Stilbenes by Wittig Reaction in a Solid-Liquid Two-Phases System," Tetrahedron Letters, vol. 37, No. 24, pp. 4225-4228 (1996).

M. Mikolajczyk et al., "Synthesis of α,β-Unsaturated Sulphides, Sulphoxides, and Sulphones by the Horner-Wittig Reaction in Two-Phase System Catalysed by Quaternary Ammonium Salts and Crown Ethers," Synthesis, pp. 278-280 (1975).

Izv. Akad. Nauk SSSR, Khim., 1990, pp. 2544-2550.

Izv. Akad. Nauk SSSR, Khim., 1988, pp. 2382-2385.

Izv. Akad. Nauk SSSR, Khim., 1988, pp. 2377-2382.

R.N. Gedye et al., "The Stereochemistry of the Wittig Reactions of Allylic Phosphroranes and Phosponate Esters with Aldehydes," Can. J. Chem., vol. 55, pp. 1218-1228 (1977).

K. Ashizawa et al., "The Crystal Structure of 3,7,11,15-Tetramethyl-2,4,6,10,14- All Trans-Hexadecapentaenoic Acid (E-5166)," Chem. Pharm. Bull., vol. 33, No. 7, pp. 3062-3064 (1985).

English language Abstract of JP 56-140949.

English language Abstract of JP 57-106638.

New Eng. J. Med., 1996, vol. 334, No. 24, pp. 1561-1567.

New Eng. J. Med., 1999, vol. 340, No. 13, pp. 1046-1047.

J. Chem. Soc. (C), 1966, pp. 2154-2165.

English Language Abstract of JP 56-140949.

English Language Abstract of JP 10-167960.

English Language Abstract JP 55-22645.

English Language Abstract of JP 58-109415.

English Language Abstract of JP 63-166824.

English Language Abstract of JP 62-77317.

English Language Abstract of JP 54-46821.

English Language of JP 55-138457.

\* cited by examiner

SOFT CAPSULE PREPARATION

TECHNICAL FIELD

The present invention relates to a soft capsule preparation with long-term stability which comprises (2E,4E,6E,10E)-3,7,11,15-tetramethyl-2,4,6,10,14-hexadecapentaenoic acid useful as a medicament for suppressing recurrence of hepatoma.

BACKGROUND ART

Prognosis of hepatoma is extremely poor, because recurrence is observed at a yearly ratio of about 25% after therapeutic treatment. Accordingly, one of outstanding important objects is prevention of recurrence of hepatoma, as well as early detection and therapy of hepatoma. (2E,4E,6E,10E)-3,7,11,15-Tetramethyl-2,4,6,10,14-hexadecapentaenoic acid (hereinafter sometimes abbreviated as "NIK-333" in the specification) is known as a compound having effects on delay or prevention of recurrence after therapeutic treatment of hepatoma. Muto et al. reported that, throughout a one-year oral administration of NIK-333 to patients after therapeutic treatment of hepatoma, the compound was revealed to have a high safety and suppress recurrence of hepatoma, thereby increased survival rate of the patients (New Eng. J. Med., 334, 1561, 1996; New Eng. J. Med., 340, 1046, 1999).

However, NIK-333 is unstable under light, heat, or oxygen, and susceptible to oxidation. Therefore, various techniques are required for preparation of pharmaceuticals. Including lipophilic vitamins as typical examples, most of lipophilic medicaments are unstable under light and heat and susceptible to oxidation, and thus various stabilization techniques are known for preparation of pharmaceuticals comprising these medicaments. As for preparation of pharmaceuticals comprising NIK-333, a method wherein a polyprenyl compound is dissolved in peanut oil to prepare a solution is disclosed in Japanese Patent Publication (Kokoku) (Sho) No 63-32058 (1988), and a pharmaceutical preparation formulated by filling NIK-333 together with peanut oil into a capsule is disclosed in Japanese Patent Unexamined Publication (Kokai) No 10-167960(1998). However, the pharmaceutical preparations obtained by these methods still have a problem of instability and are not satisfactory for a practical use.

DISCLOSURE OF THE INVENTION

An object of the present invention is to provide a soft capsule preparation with long-term stability which comprises NIK-333.

The inventors of the present invention conducted various researches to provide a NIK-333 soft capsule preparation with long-term stability. As a result, they found that the above object was achievable by dispersing NIK-333 in a vegetable oil and filling the resulting dispersion in a soft capsule having a light blocking effect. The present invention was achieved on the basis of these findings.

The present invention thus provides a soft capsule preparation which comprises a dispersion of (2E,4E,6E,10E)-3,7,11,15-tetramethyl-2,4,6,10,14-hexadecapentaenoic acid in a vegetable oil filled in a soft capsule comprising a shell having a light blocking effect.

According to a preferred embodiment of the present invention, provided are: the aforementioned soft capsule preparation, wherein the dispersion comprises a surfactant; the aforementioned soft capsule preparation, wherein the vegetable oil has an iodine value of higher than 100; the aforementioned soft capsule preparation, wherein the vegetable oil is a soybean oil or a sesame oil; the aforementioned soft capsule preparation, wherein the shell having the light blocking effect comprises a light blocking agent; the aforementioned soft capsule preparation, wherein the light blocking agent is titanium oxide and/or yellow ferric oxide; the aforementioned soft capsule preparation, wherein the shell consists of succinyl gelatin; and the aforementioned soft capsule preparation, wherein the surfactant is one or more surfactants selected from the group consisting of glycerol monostearate, sorbitan sesquioleate, polyoxyethylene sorbitan monooleate, and sucrose fatty acid ester.

BEST MODE FOR CARRYING OUT THE INVENTION (2E,4E,6E,10E)-3,7,11,15-Tetramethyl-2,4,6,10,14-hexadecapentaenoic acid is a known substance disclosed in Japanese Patent Publication (Kokoku) No. (Sho) 63-32058 (1988) and J. Chem. Soc. (c), 2154, 1966, and readily available to those skilled in the art.

As the vegetable oil, natural vegetable oils derived from plants may be used, or modified oils obtained by modification of natural vegetable oils, or synthesized oils having similar properties to those of natural vegetable oils or modified oils may be used. Typical examples of the vegetable oils include soybean oil, cottonseed oil, corn oil, safflower oil, sesame oil, coconut oil, olive oil, rape seed oil, and the like. As the vegetable oil, oils having an iodine value of higher than 100, preferably an iodine value of 104 or higher are preferred, and a semidrying oil (which has an iodine value of higher than 100 and less than 130) or a drying oil (which has an iodine value of 130 or higher) is preferred. A nondrying oil (which has an iodine value of 100 or less) may sometimes cause insufficient NIK-333 stabilization. The iodine value can be calculated by, for example, the Wijs method described in "Test method for oil and fats" of the Japanese Pharmacopoeia. The relative density of the vegetable oil is, for example, 0.914 or more, preferably 0.917 or more. An upper limit of the relative density is, for example, about 0.922. Preferably, soybean oil or sesame oil may be used. Two or more types of vegetable oils may be mixed and used. When a dispersion is prepared by dispersing NIK-333 in the vegetable oil, a surfactant can be used. Generally, surfactant is preferred to be used. As the surfactant, examples include glycerol monostearate or sorbitan sesquioleate as a low HLB surfactant, polyoxyethylene sorbitan monooleate as a high HLB surfactant, sucrose fatty acid ester, and the like. Preferably, a combination of a low HLB surfactant and a high HLB surfactant may be used. For example, a combination of polyoxyethylene sorbitan monooleate and glycerol monostearate is preferred. Although it is not intended to be bound by any specific theory, a low HLB surfactant contributes to add a thickening property and a suspension stability, and a high HLB surfactant contributes to form a dispersion in the gastrointestinal tract when the preparation is administered to a living body.

Further, a suspending agent may be used. As the suspending agent, examples include yellow beeswax or white beeswax, glycerol fatty acid esters, and hydrogenated oil.

As the shell of a soft capsule, examples include gelatin, succinyl gelatin, and the like, and succinyl gelatin is preferred to be used.

The shell having a light blocking effect can be obtained by adding a light blocking agent, which inhibits absorption of lights such as ultraviolet rays, to an ordinary shell consisting of gelatin, succinyl gelatin, and the like.

As the light blocking agent, an ordinary light blocking agent such as titanium oxide can be used. When a light blocking effect is insufficiently achieved by using only titanium oxide, other light blocking agent (for example, a coloring agent) is preferred to be used in combination. As the light blocking agent, agents which neither interact with NIK-333 nor leak in a dispersion contained in a soft capsule should be selected.

As the light blocking agent, an example includes titanium oxide, and further examples include agents conventionally used as a light blocking agent or a coloring agent, such as yellow ferric oxide, food yellow 4, food yellow 5, food red 3, food red 102, food red 105, food red 106, or red ferric oxide. In the present invention, a combination of titanium oxide and yellow ferric oxide is most preferably used.

According to the present invention, addition of concentrated glycerol or D-sorbitol as a plasticizer in the shell is often preferred.

The ratio of each ingredient in the dispersion filled in the soft capsule preparation is not particularly limited. Generally, each ingredient is used in the following range.

The vegetable oil is used in a ratio of 0.5 to 10 parts by weight, preferably 0.7 to 3 parts by weight based on NIK-333 (as 1 part by weight). The surfactant is used in a ratio of 0.05 to 0.4 parts by weight, preferably 0.02 to 0.2 parts by weight based on the vegetable oil as 1 part by weight. The light blocking agent may be used in an amount that is sufficient to almost completely inhibit the absorption of lights such as ultraviolet rays, and generally used in a ratio of 0.0005 to 0.05 parts by weight, preferably 0.001 to 0.01 parts by weight based on the shell as 1 part by weight. A particle size of NIK-333 in the dispersion is not particularly limited, and may be, for example, 30 to 50 μm.

The soft capsule preparation of the present invention can be easily prepared by filling the dispersion comprising NIK-333 inside the capsule shell by an ordinary method and sealing the capsule.

EXAMPLES

The present invention will be explained more specifically by referring to some typical examples falling within the scope of the present invention. However, the scope of the present invention is not limited to the following examples.

Example 1

(Stability Test)

NIK-333 was filled in a sealed bottle and the bottle was put into an aluminium bag. This sample was stored at 25° C., and after 0, 1, and 3 months, the peroxide values were measured. The results are shown in Table 1.

TABLE 1

|  | Storage period (month) | | |
| --- | --- | --- | --- |
|  | 0 | 1 | 3 |
| Peroxide value (meq/kg) | 0.4 | 6.2 | 14.4 |

Example 2

(Stability Test in Various Oil)

NIK-333 was dispersed in each of soybean oil, sesame oil, peanut oil, or medium chain triglyceride (MCT) (33 w/w %), and each dispersion was divided in brown vials. The air in each vial was replaced with argon gas. The dispersion was stored at 25 or 40° C., and after 0, 2, and 4 weeks, the purities were evaluated by HPLC. The results are shown in Table 2 and 3.

TABLE 2

| 25° C. storage (NIK-333 residual rate(%)) | | | |
| --- | --- | --- | --- |
|  | Storage period(week) | | |
|  | 0 | 2 | 4 |
| soybean oil | 100.0 | 100.0 | 100.0 |
| sesame oil | 100.0 | 100.1 | 99.4 |
| peanut oil | 100.0 | 99.9 | 97.1 |
| MCT | 100.0 | 67.7 | 17.5 |

TABLE 3

| 40° C. storage (NIK-333 residual rate(%)) | | | |
| --- | --- | --- | --- |
|  | Storage period (week) | | |
|  | 0 | 2 | 4 |
| soybean oil | 100.0 | 98.2 | 99.2 |
| sesame oil | 100.0 | 99.8 | 98.5 |
| peanut oil | 100.0 | 98.0 | 63.3 |
| MCT | 100.0 | 54.4 | 0.0 |

Example 3

(Preparation of a Dispersion)

| NIK-333 | 150 mg |
| --- | --- |
| polyoxyethylene sorbitan monooleate | 15 mg |
| glycerol monostearate | 6 mg |
| soybean oil | 204 mg |

Soybean oil, polyoxyethylene sorbitan monooleate, and glycerol monostearate in the above formulation were heated for dissolution, and then cooled. NIK-333 was mixed and dispersed in the mixture, and then the mixture was degassed to obtain a dispersion.

Example 4

(Preparation of a Soft Capsule Shell)

| succinyl gelatin | 134 mg |
| --- | --- |
| concentrated glycerol | 27 mg |
| D-sorbitol solution | 27 mg |
| titanium oxide | 1.3 mg |

The concentrated glycerol, D-sorbitol 70% solution, and titanium oxide in the above formulation, and water were stirred to obtain a dispersion. The dispersion was added with a solution of succinyl gelatin heated at 60° C., and stirred for dissolution. The mixture was degassed under reduced pressure and the viscosity of the mixture was adjusted by using purified water to obtain a soft capsule shell.

Example 5

(Preparation of a Soft Capsule Shell)

| succinyl gelatin | 134 mg |
| concentrated glycerol | 27 mg |
| D-sorbitol solution | 27 mg |
| titanium oxide | 0.7 mg |
| yellow ferric oxide | 0.5 mg |

A soft capsule shell was prepared in the same manner as that of Example 4, except yellow ferric oxide was used.

Example 6

(Photostability Test)

The dispersion obtained in Example 3 was filled inside the soft capsule shell obtained in Example 4 and 5 by using capsule filling machine (Leiner-manufactured rotary-type filling machine). The soft capsule preparations obtained were subjected to a photostability test (overall illumination 1.2 million lux.hr), and the NIK-333 contents were measured by HPLC to obtain residual rates.

TABLE 4

Photostability (NIK-333 residual rate(%))

| | Before irradiation | After irradiation |
| --- | --- | --- |
| Example 4 | 100.0 | 98.3 |
| Example 5 | 100.0 | 100.0 |

Example 7

(Preparation of a Pharmaceutical Composition)

| NIK-333 | 75 mg |
| polyoxyethylene sorbitan monooleate | 8 mg |
| glycerol monostearate | 3 mg |
| soybean oil | 102 mg |

A pharmaceutical composition was prepared according to the above formulation in the same manner as that of Example 3.

Example 8

(Preparation of a Soft Capsule Shell)

| succinyl gelatin | 78 mg |
| concentrated glycerol | 16 mg |
| D-sorbitol solution | 16 mg |
| titanium oxide | 0.4 mg |
| yellow ferric oxide | 0.3 mg |

A soft capsule shell was prepared according to the above formulation in the same manner as that of Example 5. A soft capsule preparation was further obtained in the same manner as that of Example 6.

Example 9

(Stability Test)

The soft capsule preparation obtained in Example 8 was stored at 25° C. and 60% relative humidity (60% RH), and at 40° C. and 75% relative humidity (75% RH), and contents and peroxide values were measured. NIK-333 contents are shown in Table 5, and the peroxide values are shown in Table 6.

TABLE 5

NIK-333 content (%)

| | Storage period (month) | | | | | |
| --- | --- | --- | --- | --- | --- | --- |
| Storage condition | 0 | 1 | 6 | 12 | 18 | 24 |
| 25° C., 60% RH | 102.5 | 100.5 | 100.8 | 100.2 | 101.2 | 100.8 |
| 40° C., 75% RH | 102.5 | 101.1 | 101.5 | — | — | — |

TABLE 6

Peroxide value (meq/kg)

| | Storage period (month) | | | | | |
| --- | --- | --- | --- | --- | --- | --- |
| Storage condition | 0 | 1 | 6 | 12 | 18 | 24 |
| 25° C., 60% RH | 0.3 | 0.5 | 0.5 | 0.6 | 0.7 | 0.8 |
| 40° C., 75% RH | 0.3 | 0.7 | 1.1 | — | — | — |

INDUSTRIAL APPLICABILITY

The soft capsule preparation of the present invention is stable even after a long-term storage, although NIK-333 is a very unstable substance.

What is claimed is:

1. A soft capsule preparation which comprises a dispersion of (2E,4E,6E,10E)-3,7,11,15-tetramethyl-2,4,6,10,14-hexadecapentaenoic acid in a vegetable oil comprising soybean oil, sesame oil, or a mixture thereof filled in a soft capsule comprising a shell having a light blocking effect.

2. The soft capsule preparation according to claim 1, wherein the dispersion comprises at least one surfactant selected from glycerol monostearate, sorbitan sesquioleate, polyoxyethylene sorbitan monooleate, and sucrose fatty acid ester.

3. The soft capsule preparation according to claim 2, wherein the at least one surfactant comprises polyoxyethylene sorbitan monooleate and glycerol monostearate.

4. The soft capsule preparation according to claim 1, wherein the shell having the light blocking effect comprises a light blocking agent.

5. The soft capsule preparation according to claim 4, wherein the light blocking agent is titanium oxide, yellow ferric oxide, or a mixture thereof.

6. The soft capsule preparation according to claim 1, wherein the shell comprises of succinyl gelatin.

* * * * *